US012169788B2

(12) United States Patent
Coles et al.

(10) Patent No.: US 12,169,788 B2
(45) Date of Patent: Dec. 17, 2024

(54) ANALYSIS OF NEUROLOGICAL CONDITIONS, INCLUDING PREDICTION OF FUTURE SEIZURE EVENTS AND/OR DETECTION OF CURRENT SEIZURE EVENTS, BASED ON ANALYSIS OF BLEPHAROMETRIC DATA

(71) Applicant: SDIP HOLDINGS PTY LTD, Victoria (AU)

(72) Inventors: Scott Coles, Queenscliff (AU); Trefor Morgan, Queenscliff (AU)

(73) Assignee: SDIP HOLDINGS PTY LTD, Victoria (AU)

( * ) Notice: Subject to any disclaimer, the term of this patent is extended or adjusted under 35 U.S.C. 154(b) by 716 days.

(21) Appl. No.: 17/287,882

(22) PCT Filed: Oct. 23, 2019

(86) PCT No.: PCT/AU2019/051156
§ 371 (c)(1),
(2) Date: Apr. 22, 2021

(87) PCT Pub. No.: WO2020/082123
PCT Pub. Date: Apr. 30, 2020

(65) Prior Publication Data
US 2021/0345937 A1  Nov. 11, 2021

(30) Foreign Application Priority Data
Oct. 23, 2018 (AU) .................................. 2018904026
Oct. 23, 2018 (AU) .................................. 2018904027
(Continued)

(51) Int. Cl.
*G06V 20/59* (2022.01)
*A61B 3/113* (2006.01)
(Continued)

(52) U.S. Cl.
CPC ................ *G06N 5/04* (2013.01); *A61B 3/113* (2013.01); *A61B 3/14* (2013.01); *A61B 5/004* (2013.01);
(Continued)

(58) Field of Classification Search
USPC ................ 382/100–159, 168–224, 254–305; 706/1–62, 900–903
See application file for complete search history.

(56) References Cited

U.S. PATENT DOCUMENTS 6,246,344 B1 * 6/2001 Torch ..................... A61B 5/163
341/173
7,071,831 B2 7/2006 Johns
(Continued)

FOREIGN PATENT DOCUMENTS

WO  2015030797 A1  3/2015

OTHER PUBLICATIONS

Johns Murray; Measuring Alertness; Sep. 8, 2006 (Year: 2006).*
(Continued)

*Primary Examiner* — Marcellus J Augustin
(74) *Attorney, Agent, or Firm* — TraskBritt

(57) ABSTRACT

Blepharometric data (data describing eyelid position as a function of time) is recorded and processed for the purposes of predicting a future risk and/or current occurrence of neurological events such as seizures. For example, in one embodiment, blepharometric data is recorded via infrared reflectance oculography spectacles, and processed in real time thereby to extract a set of blepharometric artifacts. Where those artifacts indicate prolonged spiking in blink calmness (for example, based on spiking in negative inter-event duration, or negative IED), an alert is able to be generated thereby to indicate that the subject is at risk of a seizure in a proximal time period. This provides an oppor-
(Continued)

tunity to implement mitigation measures, for example, to reduce the likelihood of the seizure manifesting, and/or to mitigate harm should the seizure occur.

17 Claims, 9 Drawing Sheets

(30) Foreign Application Priority Data

| Oct. 23, 2018 | (AU) | ................................ | 2018904028 |
|---|---|---|---|
| Oct. 27, 2018 | (AU) | ................................ | 2018904076 |
| Nov. 8, 2018 | (AU) | ................................ | 2018904312 |
| Jan. 25, 2019 | (AU) | ................................ | 2019900229 |

(51) Int. Cl.

| A61B 3/14 | (2006.01) |
|---|---|
| A61B 5/00 | (2006.01) |
| A61B 5/11 | (2006.01) |
| A61B 5/18 | (2006.01) |
| B60W 40/08 | (2012.01) |
| G06F 18/214 | (2023.01) |
| G06N 5/04 | (2023.01) |
| G06T 7/00 | (2017.01) |
| G06V 10/40 | (2022.01) |
| G06V 40/18 | (2022.01) |
| G16H 40/63 | (2018.01) |
| G16H 50/20 | (2018.01) |

(52) U.S. Cl.
CPC .......... *A61B 5/0077* (2013.01); *A61B 5/1103* (2013.01); *A61B 5/1118* (2013.01); *A61B 5/1128* (2013.01); *A61B 5/18* (2013.01); *A61B 5/4094* (2013.01); *A61B 5/4842* (2013.01); *A61B 5/6803* (2013.01); *A61B 5/6893* (2013.01); *A61B 5/7275* (2013.01); *A61B 5/7282* (2013.01); *A61B 5/746* (2013.01); *B60W 40/08* (2013.01); *G06F 18/214* (2023.01); *G06T 7/0012* (2013.01); *G06V 10/40* (2022.01); *G06V 20/597* (2022.01); *G06V 40/193* (2022.01); *G16H 40/63* (2018.01); *G16H 50/20* (2018.01); *A61B 2560/02* (2013.01); *B60W 2040/0872* (2013.01); *B60W 2540/221* (2020.02); *B60W 2540/223* (2020.02); *G06T 2207/20081* (2013.01); *G06T 2207/30041* (2013.01); *G06T 2207/30201* (2013.01); *G06T 2207/30268* (2013.01)

(56) References Cited

U.S. PATENT DOCUMENTS

| 7,791,491 | B2 | 9/2010 | Johns |
|---|---|---|---|
| 7,815,311 | B2 | 10/2010 | Johns et al. |
| 9,207,760 | B1 | 12/2015 | Wu et al. |
| 12,042,294 | B2 | 7/2024 | Krueger |
| 2011/0077548 | A1* | 3/2011 | Torch ................... A61B 5/165 600/558 |
| 2011/0216181 | A1 | 9/2011 | Yoda et al. |
| 2011/0295142 | A1* | 12/2011 | Chakravarthy ...... A61B 5/7203 600/544 |
| 2011/0313259 | A1 | 12/2011 | Hatakeyama et al. |
| 2012/0072121 | A1 | 3/2012 | Mollicone et al. |
| 2012/0083700 | A1 | 4/2012 | Osorio |
| 2013/0022948 | A1 | 1/2013 | Angell et al. |
| 2013/0184997 | A1 | 7/2013 | Mott |
| 2013/0215390 | A1 | 8/2013 | Johns et al. |
| 2016/0019410 | A1 | 1/2016 | Komogortsev |
| 2016/0073874 | A1* | 3/2016 | Tsai ...................... A61B 5/398 351/210 |
| 2016/0213298 | A1 | 7/2016 | Elsmore et al. |
| 2016/0216298 | A1 | 7/2016 | Campeanu et al. |
| 2017/0119248 | A1 | 5/2017 | Morgan et al. |
| 2017/0135577 | A1 | 5/2017 | Komogortsev |
| 2017/0337438 | A1 | 11/2017 | El et al. |
| 2018/0247141 | A1 | 8/2018 | Mori |
| 2021/0378568 | A1 | 12/2021 | Coles et al. |
| 2022/0254461 | A1 | 8/2022 | Vaughan |

OTHER PUBLICATIONS

Burton David; Mobile Wearable Monitoring Systems; 2016 (Year: 2016).*
Nicolosi Robert; Botulinum Nanoemulsions; 2008 (Year: 2008).*
Da Conceicao et al., Blinking and Eyelid Myoclonia: Characteristics and Correlations of Eyelid Movements, Seizure, vol. 24, (2015(, pp. 12-16.
Jiang et al., Capturing and Evaluating Blinks from Video-Based Eyetrackers, Behav. Res. (2013), vol. 45, pp. 656-663.
Man Dal et al., Towards Detection of Bus Driver Fatigue Based on Robust Visual Analysis of Eye State, IEEE Transactions, vol. 18, No. 3, Mar. 2017, 545-557.
Noman et al., Mobile-Based Eye-Blink Detection Performance Analysis on Android Platform, www.frontiersin.org, (Mar. 2018), vol. 5, Article 4, pp. 1-11.
Paprocki et al., What Does Eye-Blink Rate Variability Dynamics Tess Us About Cognitive Performance, Frontiers in Human Neuroscience, (Dec. 2017), vol. 11, Article 620, 99.1-9.
Siegle et al., Blink Before and After you Think: Blinks Occur Prior to and Following Cognitive Load is Indexed by Pupillary Responses, Psychophysiology, 45, (2008), pp. 679-687.
International Search Report for International Application No. PCT/AU2019/051156 dated Feb. 7, 2020, 7 pages.
International Written Opinion for International Application No. PCT/AU2019/051156 dated Feb. 7, 2020, 9 pages.
Byrom et al. "Brain Monitoring Devices in Neuroscience Clinical Research: The Potential of Remote Monitoring Using Sensors, Wearables, and Mobile Devices." Clinical Pharmacology & Therapeutics, (Online Apr. 18), vol. 104, No. 1., pp. 59-71. (Year: 2018).
IEEE (Towards Detection of Bus Driver Fatigue Based on Robust Visual Analysis of Eye State, Bappaditya Mandal, Liyuan Li, Gang Sam Wang, and Jie Lin, Mar. 2017) (Year: 2017).
Suzuki et al. "Measurement of Driver's Consciousness by Image Processing—A Method for Presuming Driver's Drowsiness by Eye-Blinks coping with Individual Differences." IEEE International Conference on Systems, Man and Cybernetics, Taipei, Taiwan, doi: 10.1109/ICSMC.2006.385313, pp. 2891-2896. (Year: 2006).

* cited by examiner

ANALYSIS OF NEUROLOGICAL CONDITIONS, INCLUDING PREDICTION OF FUTURE SEIZURE EVENTS AND/OR DETECTION OF CURRENT SEIZURE EVENTS, BASED ON ANALYSIS OF BLEPHAROMETRIC DATA

CROSS-REFERENCE TO RELATED APPLICATIONS

This application is a national phase entry under 35 U.S.C. § 371 of International Patent Application PCT/AU2019/051156, filed Oct. 23, 2019, designating the United States of America and published as International Patent Publication WO 2020/082123 A1 on Apr. 30, 2020, which claims the benefit under Article 8 of the Patent Cooperation Treaty to Australian Patent Application Serial No. 2018904026, filed Oct. 23, 2018, Australian Patent Application Serial No. 2018904027, filed Oct. 23, 2018, Australian Patent Application Serial No. 2018904028, filed Oct. 23, 2018, Australian Patent Application Serial No. 2018904076, filed Oct. 27, 2018, Australian Patent Application Serial No. 2018904312, filed Nov. 8, 2018, and Australian Patent Application Serial No. 2019900229, filed Jan. 25, 2019.

TECHNICAL FIELD

The present disclosure relates to, in various embodiments, analysis of neurological conditions using blepharometric data (data representative of eyelid movement parameters). For example, some embodiments provide methods and associated technology that enable advanced prediction of a seizure event in a human subject, or an increased risk of such a seizure event. Other embodiments allow for real-time detection of certain forms of seizure event. While some embodiments will be described herein with particular reference to such applications, it will be appreciated that the present disclosure is not limited to such a field of use, and is applicable in broader contexts.

BACKGROUND

Any discussion of the background art throughout the specification should in no way be considered as an admission that such art is widely known or forms part of common general knowledge in the field.

It is known to analyze some neurological conditions from analysis of blepharometric movements. For example, U.S. Pat. No. 7,791,491 teaches a method and apparatus for measuring the neurological condition of drowsiness based on the amplitude to velocity ratio for eyelids closing and opening during blinking as well as measuring duration of opening and closing. This enables an objective measurement of drowsiness. However, beyond investigations into drowsiness, alertness, and other similar conditions, there has been limited application of analysis of blepharometric movements for more complex neurological conditions.

The present inventors, through their research into relationships between eyelid movement parameters and neurological conditions, have identified opportunities for detection and/or prediction of additional neurological conditions via analysis of eyelid movement parameters.

BRIEF SUMMARY

It is an object of the present disclosure to overcome or ameliorate at least one of the disadvantages of the prior art, or to provide a useful alternative.

One embodiment provides a computer-implemented method for performing prediction of a future seizure event for a human subject, the method including:
  receiving, as input, data derived from a sensor device that is operated to detect eyelid movements for a human subject;
  processing the input data thereby to determine a series of values representative of eyelid movement calmness, wherein eyelid movement calmness is derived from a measure representative of eyelid movement during a detected blink event
  identifying, in the determined series of values representative of eyelid movement calmness, a threshold increase in eyelid movement calmness characteristics over a defined period of time; and
  in response to identification of the threshold increase in eyelid movement calmness characteristics, providing an output signal representative of future seizure event prediction.

One embodiment provides a computer-implemented method wherein eyelid movement calmness is derived from measurements of negative IED.

One embodiment provides a computer-implemented method wherein negative IED trends toward Blink Total Duration (BTD) as eyelid movement calmness increases.

One embodiment provides a computer-implemented method wherein calmness is derived from measurements of eyelid movement between a detected blink eyelid closure event and a subsequent blink eyelid opening event.

One embodiment provides a computer-implemented method wherein threshold eyelid movement calmness is represented by observation of below a threshold of eyelid movement between a detected blink eyelid closure event and a subsequent blink eyelid opening event.

One embodiment provides a computer-implemented method wherein identifying, in the determined series of values representative of eyelid movement calmness, a threshold increase in eyelid movement calmness characteristics includes: determining a baseline eyelid movement calmness periodic value for the subject, and identifying a threshold deviation from the baseline eyelid movement calmness periodic value for the subject.

One embodiment provides a computer-implemented method wherein the threshold deviation is represented by detection of a threshold number of spikes in blink calmness measurements in a defined period.

One embodiment provides a computer-implemented method wherein identifying, in the determined series of values representative of negative IED, a threshold increase in negative IED characteristics includes: determining a baseline negative IED periodic value for the subject, and identifying a threshold deviation from the baseline negative IED periodic value for the subject.

One embodiment provides a computer-implemented method wherein the threshold deviation is represented by detection of a threshold number of spikes in negative IED in a defined period.

One embodiment provides a computer-implemented method wherein the baseline negative IED periodic value for the subject is defined by an average IED value over a defined time period, and the threshold deviation is equal to or greater than 30%.

One embodiment provides a computer-implemented method wherein the defined time period is between 5 minutes and 20 minutes.

One embodiment provides a computer-implemented method including identifying presence of an additional artifact in blepharometric data, wherein the step of (in response to identification of the threshold increase in negative IED characteristics) providing an output signal representative of future seizure event prediction, is performed only in the case that the additional artifact is identified.

One embodiment provides a computer-implemented method wherein identifying, in the determined series of values representative of negative IED, a threshold increase in IED characteristics includes: in a period of between about 300 seconds and 1,200 seconds, identifying between 3 and 6 negative IEDs of greater than 3000 milliseconds.

One embodiment provides a computer-implemented method wherein identifying, in the determined series of values representative of negative IED, a threshold increase in negative IED characteristics includes: maintaining a rolling count of negative IEDs over a defined threshold value for a predefined preceding period, and determine the threshold increase in the case that the count exceeds a predefined value.

One embodiment provides a computer-implemented method wherein the threshold value is 200% of a calculated baseline average negative IED value.

One embodiment provides a computer-implemented method wherein the predefined preceding period is between eight minutes and fifteen minutes, and wherein the count is equal to or greater than four.

One embodiment provides a computer-implemented method wherein the method includes operating a set of infrared reflectance oculography spectacles thereby to provide the sensor device.

One embodiment provides a computer-implemented method wherein the method is performed by a processing unit that is communicatively coupled to the spectacles.

One embodiment provides a computer-implemented method wherein the method includes operating an image processing system that is configured to: (i) detect a human's eye region in image data; and (ii) measure attributes of blinks for that human by analysis of the image data; thereby to provide the sensor device.

One embodiment provides a computer-implemented method wherein a filtering process is applied thereby to identify voluntary blinks, and exclude voluntary blinks from consideration in data processing.

One embodiment provides a device including:
a sensor system configured to perform monitoring of a human subject's eye region, thereby to detect and measure attributes of blinks;
a processing system configured of process the measured attributes of blinks thereby to monitor a metric of inter-event duration (IED); and
an output system configured to provide an alert in the case that there is a threshold deviation in the monitored metric of IED.

One embodiment provides a computer-implemented method for performing prediction of a future seizure event for a human subject, the method including:
receiving, as input, data derived from a sensor device that is operated to detect eyelid movements for a human subject;
processing the input data thereby to determine onset of a threshold periodic statistical variation from a baseline value for one or more blepharometric artifact attributes; and
in response to identification of the onset of the threshold periodic statistical variation from a baseline value for one or more blepharometric artifact attributes, providing an output signal representative of future seizure event prediction.

One embodiment provides a method wherein the threshold periodic statistical variation includes identification of spiking in eyelid movement calmness attributes.

One embodiment provides a method wherein the threshold periodic statistical variation includes identification of spiking in inter-event duration (IED).

One embodiment provides a portable electronic device including:
a display screen; and
a front-facing camera;
wherein the portable electronic device is configured to concurrently execute: (i) a first software application that provides data via the display screen; and (ii) a second software application that receives input from the front facing camera thereby to facilitate detection and analysis of blepharometric data.

One embodiment provides a device wherein the first software application is a messaging application.

One embodiment provides a device wherein the first software application is a social media application.

One embodiment provides a computer-implemented method for performing detection of a seizure event for a human subject, the method including:
receiving an input signal from blepharometric monitoring hardware, wherein the input signal is representative of eyelid position against time;
processing the input signal thereby to identify myoclonic eyelid movement having prescribed parameters; and
in the case that myoclonic eyelid movement having prescribed parameters is identified, causing output of a warning signal representative of detection of a possible seizure event.

One embodiment provides a computer-implemented method wherein the prescribed parameters include:
(i) a blink rate above a defined threshold
(ii) the blink rate sustained above the defined threshold for a defined period; and
(iii) eyelid position having defined attributes for the defined period.

One embodiment provides a computer-implemented method wherein the defined threshold is greater than one blink per second.

One embodiment provides a computer-implemented method wherein the defined threshold is above 1.5 blinks per second.

One embodiment provides a computer-implemented method wherein the defined period is greater than or equal to 2 seconds.

One embodiment provides a computer-implemented method wherein the defined period is greater than or equal to 3 seconds.

One embodiment provides a computer-implemented method wherein the defined period is greater than or equal to 4 seconds.

One embodiment provides a computer-implemented method wherein the defined attributes are a maximum eyelid closure of 50%.

One embodiment provides a computer-implemented method wherein the defined attributes are an average eyelid position of greater than 70% closure.

One embodiment provides a computer-implemented method wherein the method includes operating a set of infrared reflectance oculography spectacles thereby to provide the input signal.

One embodiment provides a computer-implemented method wherein the method is performed by a processing unit that is communicatively coupled to the spectacles.

One embodiment provides a computer-implemented method wherein the method includes operating an image processing system that is configured to: (i) detect a human's eye region in image data; and (ii) measure attributes of eyelid movement for that human by analysis of the image data; thereby to provide the input signal.

One embodiment provides a computer-implemented method wherein a filtering process is applied thereby to identify voluntary blinks, and exclude voluntary blinks from consideration in data processing.

One embodiment provides a device including:
- a sensor system configured to perform monitoring of a human subject's eye region, thereby to detect and measure attributes of blinks;
- a processing system configured of process the measured attributes of blinks thereby to monitor for myoclonic eyelid movement having prescribed parameters; and
- an output system configured to provide a possible seizure detection alert in the case that myoclonic eyelid movement having prescribed parameters is identified.

One embodiment provides a device wherein the prescribed parameters include:
(i) a blink rate above a defined threshold
(ii) the blink rate sustained above the defined threshold for a defined period; and
(iii) eyelid position having defined attributes for the defined period.

One embodiment provides a device wherein the defined threshold is greater than one blink per second.

One embodiment provides a device wherein the defined threshold is above 1.5 blinks per second.

One embodiment provides a device wherein the defined period is greater than or equal to 2 seconds.

One embodiment provides a device the defined period is greater than or equal to 3 seconds.

One embodiment provides a device wherein the defined period is greater than or equal to 4 seconds.

One embodiment provides a device wherein the defined attributes are a maximum eyelid closure of 50%.

One embodiment provides a device wherein the defined attributes are an average eyelid position of greater than 70% closure.

One embodiment provides a system for providing warning of a change in neurological conditions, the system including:
- a sensor system configured to perform monitoring of a human subject's eye region, thereby to detect and measure attributes of blinks;
- a processing system configured of process the measured attributes of blinks thereby to monitor a metric of eyelid movement calmness; and
- an output system configured to provide an alert in the case that there is a threshold deviation in the monitored metric of IED.

One embodiment provides a system wherein the measure of eyelid movement event calmness is derived from measurements of negative Inter-Event Duration (IED).

One embodiment provides a system wherein the alert includes an alert representative of a risk of an upcoming seizure event.

One embodiment provides a computer-implemented method for performing prediction of a possible future seizure event for a human subject, the method including:
  receiving, as input, data derived from a sensor device that is operated to detect eyelid movements for a human subject;
  processing the input data thereby to determine a series of values representative of eyelid movement calmness, wherein eyelid movement calmness is derived from a measure representative of eyelid movement during a detected blink event
  identifying, in the determined series of values representative of eyelid movement calmness, a threshold increase in eyelid movement calmness characteristics over a defined period of time; and
  in response to identification of the threshold increase in eyelid movement calmness characteristics, providing an output signal representative of future seizure event prediction.

One embodiment provides a system for providing warning of a change in neurological conditions, the system including:
  a sensor system configured to perform monitoring of a human subject's eye region, thereby to detect and measure attributes of blinks;
  a processing system configured of process the measured attributes of blinks thereby to monitor a metric of eyelid movement calmness; and
  an output system configured to provide an alert in the case that there is a threshold deviation in the monitored metric of IED.

One embodiment provides a system wherein the measure of eyelid movement event calmness is derived from measurements of negative Inter-Event Duration (IED).

One embodiment provides a system wherein the alert includes an alert representative of a risk of an upcoming seizure event.

One embodiment provides a method for performing prediction of a possible future seizure event for a human subject, the method including:
  receiving, as input, data derived from a sensor device that is operated to detect eyelid movements for a human subject;
  processing the input data thereby to determine a series of values representative of eyelid movement calmness, wherein eyelid movement calmness is derived from a measure representative of eyelid movement during a detected blink event
  identifying, in the determined series of values representative of eyelid movement calmness, a threshold increase in eyelid movement calmness characteristics over a defined period of time; and
  in response to identification of the threshold increase in eyelid movement calmness characteristics, providing an output signal representative of future seizure event prediction.

One embodiment provides a method wherein eyelid movement calmness is derived from measurements of negative IED.

One embodiment provides a method wherein negative IED trends toward Blink Total Duration (BTD) as eyelid movement calmness increases.

One embodiment provides a method wherein calmness is derived from measurements of eyelid movement between a detected blink eyelid closure event and a subsequent blink eyelid opening event.

One embodiment provides a method wherein threshold eyelid movement calmness is represented by observation of below a threshold of eyelid movement between a detected blink eyelid closure event and a subsequent blink eyelid opening event.

One embodiment provides a method wherein identifying, in the determined series of values representative of eyelid movement calmness, a threshold increase in eyelid movement calmness characteristics includes: determining a baseline eyelid movement calmness periodic value for the subject, and identifying a threshold deviation from the baseline eyelid movement calmness periodic value for the subject.

One embodiment provides a method wherein the threshold deviation is represented by detection of a threshold number of spikes in blink calmness measurements in a defined period.

One embodiment provides a method wherein identifying, in the determined series of values representative of negative IED, a threshold increase in negative IED characteristics includes: determining a baseline negative IED periodic value for the subject, and identifying a threshold deviation from the baseline negative IED periodic value for the subject.

One embodiment provides a method wherein the threshold deviation is represented by detection of a threshold number of spikes in negative IED in a defined period.

One embodiment provides a method wherein the baseline negative IED periodic value for the subject is defined by an average IED value over a defined time period, and the threshold deviation is equal to or greater than 30%.

One embodiment provides a method wherein the defined time period is between 5 minutes seconds and 20 minutes.

One embodiment provides a method including identifying presence of an additional artifact in blepharometric data, wherein the step of (in response to identification of the threshold increase in negative IED characteristics) providing an output signal representative of future seizure event prediction is performed only in the case that the additional artifact is identified.

One embodiment provides a method wherein identifying, in the determined series of values representative of negative IED, a threshold increase in IED characteristics includes: in a period of between about 300 seconds and 1,200 seconds, identifying between 3 and 6 negative IEDs of greater than 3000 milliseconds.

One embodiment provides a method for performing prediction of a future seizure event for a human subject, the method including:
receiving, as input, data derived from a sensor device that is operated to detect eyelid movements for a human subject;
processing the input data thereby to determine onset of a threshold periodic statistical variation from a baseline value for one or more blepharometric artifact attributes; and
in response to identification of the onset of the threshold periodic statistical variation from a baseline value for one or more blepharometric artifact attributes, providing an output signal representative of future seizure event prediction.

One embodiment provides a method wherein the threshold periodic statistical variation includes identification of spiking in eyelid movement calmness attributes.

One embodiment provides a method wherein the threshold periodic statistical variation includes identification of spiking in inter-event duration (IED).

One embodiment provides a method including: capturing measurements of attributes of a human subject's eyelid movement; and based on those measurements, identifying an increased risk of a future seizure event.

One embodiment provides a computer-implemented method for performing detection of a seizure event for a human subject, the method including:
receiving an input signal from blepharometric monitoring hardware, wherein the input signal is representative of eyelid position against time;
processing the input signal thereby to identify myoclonic eyelid movement having prescribed parameters; and
in the case that myoclonic eyelid movement having prescribed parameters is identified, causing output of a warning signal representative of detection of a possible seizure event.

One embodiment provides a method wherein the prescribed parameters include:
(i) a blink rate above a defined threshold
(ii) the blink rate sustained above the defined threshold for a defined period; and
(iii) eyelid position having defined attributes for the defined period.

One embodiment provides a method including:
a sensor system configured to perform monitoring of a human subject's eye region, thereby to detect and measure attributes of blinks;
a processing system configured of process the measured attributes of blinks thereby to monitor for myoclonic eyelid movement having prescribed parameters; and
an output system configured to provide a possible seizure detection alert in the case that myoclonic eyelid movement having prescribed parameters is identified.

One embodiment provides a method wherein the prescribed parameters include:
(i) a blink rate above a defined threshold
(ii) the blink rate sustained above the defined threshold for a defined period; and
(iii) eyelid position having defined attributes for the defined period.

Reference throughout this specification to "one embodiment," "some embodiments" or "an embodiment" means that a particular feature, structure or characteristic described in connection with the embodiment is included in at least one embodiment of the present disclosure. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms "comprising," "comprised of," or "which comprises" is an open term that means including at least the elements/features that follow, but not excluding others. Thus, the term "comprising," when used in the claims, should not be interpreted as being limitative to the means or elements or steps listed thereafter. For example, the scope of the expression a device comprising A and B should not be limited to devices consisting only of elements A and B. Any one of the terms "including," or "which includes," or "that includes" as used herein is also an open term that also means including at least the elements/features that follow the term, but not excluding others. Thus, "including" is synonymous with and means "comprising."

As used herein, the term "exemplary" is used in the sense of providing examples, as opposed to indicating quality. That is, an "exemplary embodiment" is an embodiment provided as an example, as opposed to necessarily being an embodiment of exemplary quality.

BRIEF DESCRIPTION OF THE DRAWINGS

Embodiments of the present disclosure will now be described, by way of example only, with reference to the accompanying drawings in which.

DETAILED DESCRIPTION

Figure 1:
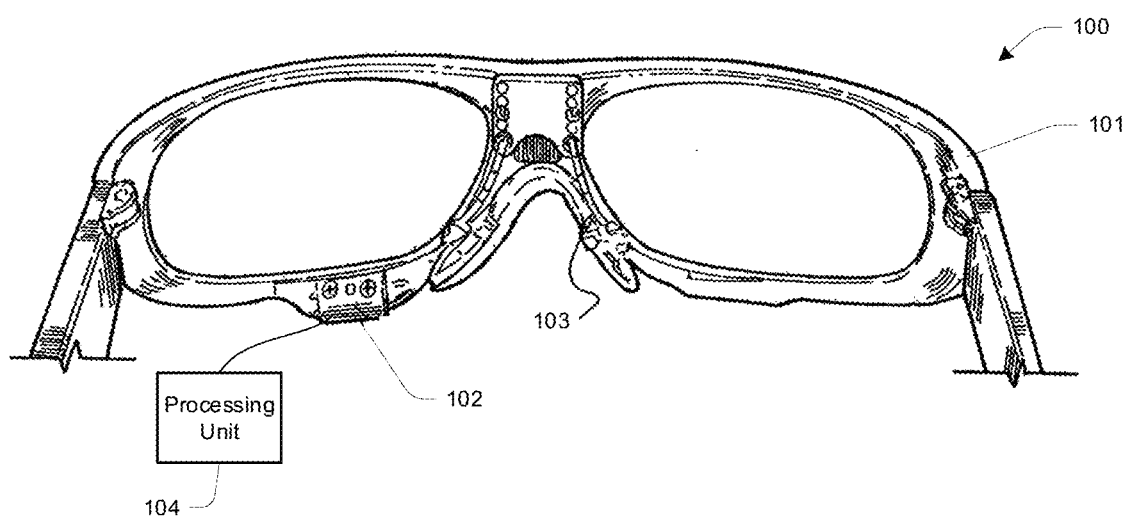
FIG. 1 illustrates a blepharometric detection system according to one embodiment.

The present disclosure relates, in various embodiments, to detection and/or prediction of neurological conditions on analysis of involuntary eyelid (blepharon) movement parameters. For example, some embodiments provide methods and associated technology that enable advanced (i.e., "ahead of time") prediction of a seizure event in a human subject. Embodiments described herein include hardware devices (for example, wearable units, in-vehicle monitoring devices, and others) that are configured to collect blepharometric data from a human subject, and provide an alert in the case that analysis of this data indicates that a seizure event is likely to occur. Further embodiments find application for purposes other than seizure prediction, for example, real-time seizure detection.

Examples are described below primarily by reference to seizure prediction and seizure detection. In the context of seizure prediction, the term "prediction" is used to describe a process whereby technology is able to make an autonomous determination that a person is at risk of a potential seizure in a proximal time period (for example, within an hour). This allows for preventative and/or risk management measures to be implemented (for example, medication, or refraining from driving or operating machinery). In the context of seizure detection, it is known to use technology to detect seizure events in human subjects, for example, using accelerometers and the like. Such technology, however, is generally limited to detection of convulsive seizures. The technology described below is especially significant in the context of detecting non-convulsive seizures (or "absence seizures"), in respect of which a lack of muscu-loskeletal symptoms restricts efficacy of existing technology. However, the technology is not limited to identification of non-convulsive/absence seizures, and may be applicable in other seizure types.

A human subject's involuntary blinks and eyelid movements are influenced by a range of factors, including the subject's behavioral state and brain function. For example, this has been used in the past for detection of drowsiness. More broadly, analysis of data derived from eyelid movements can be performed thereby to identify data artifacts, patterns and the like, and these are reflective of the subject's behavioral state, brain function and the like.

The embodiments described below refer to analysis of blepharometric data. The term "blepharometric data" refers to data that describes movements of a human subject's eyelid (or eyelids). Eyelid movements are commonly categorized as "blinks" or "partial blinks." The term "blepharometric data" is used to distinguish technology described herein from other technologies that detect the presence of blinks for various purposes. The technology herein is focused on analyzing eyelid movement as a function of time, typically measured as an amplitude. This data may be used to infer the presence of what would traditionally be termed "blinks," however it is attributes of "events" and other parameters identifiable in eyelid movements that are of primary interest to technologies described herein. These are referred to as "blepharometric artifacts," with such artifacts being identifiable by application of various processing algorithms to a data set that described eyelid position as a function of time (i.e., blepharometric data). For example, the artifacts may include:

Blink total duration (BTD), which is preferably measured as a time between commencement of closure movement that exceeds a defined threshold and completion of subsequent opening movement, Blink rates, Amplitude to velocity ratios (AVRs), Negative Inter-Event-Duration (IED) (discussed in detail further below), Positive IED, Negative AVR (i.e., during closure), Positive AVR (i.e., during re-opening), AVR Product (negative AVR*positive AVR), AVR ratio (negative AVR divided by positive AVR), BECD (blink eye closure duration), Negative DOQ (duration of ocular quiescence), Positive DOQ, Relative Amplitude, Relative Position, Max Amplitude, Max Velocity, Neg ZCI (zero crossing index), Pos ZCI, Blink start position, Blink end position, Blink start time, Blink end time, and Trends and changes in any of the above artifacts over a defined period.

In terms of behavioral state, there are many factors that have an effect on involuntary blepharometric movements, with examples including: a subject's state of physical activity; a subject's posture; other aspects of a subject's positional state; subject movement; subject activity; how well slept the subject happens to be; levels of intoxication and/or impairment; and others. In terms of brain function, factors that have effects on involuntary blepharometric movements include degenerative brain injuries (e.g., Parkinson's disease) and traumatic brain injuries.

For embodiments disclosed below, various forms of eyelid monitoring hardware may be used. A range of devices are known in the art, including devices that make use of electrodes, devices that make use of infrared reflectance oculography, and devices that make use of image capture modules in combination with image processing algorithms that are configured to identify a subject's eye movements. Specific reference is made in the examples below to a hardware arrangement including spectacles containing IR sensing componentry, for example, as described in U.S. Pat. No. 7,815,311. That, however, should not be considered as a limiting example, and analysis techniques described herein are optionally performed using a range of monitoring hardware arrangements, including arrangements specifically tailored/configured to identify specific eyelid movement characteristics.

In embodiments where infrared reflectance oculography techniques are used, the blepharometric data is optionally defined by a reading made by an infrared reflectance sensor, and as such is a proxy for eyelid position. That is, rather than monitoring the actual position of an eyelid, infrared reflectance oculography techniques use reflectance properties and in so doing are representative of the extent to which an eye is open (as the presence of an eyelid obstructing the eye affects reflectivity). In some embodiments, additional information beyond eyelid position may be inferred from infrared reflectance oculography, for example, whether a subject is undergoing tonic eye movement. For the present purposes, "blepharometric data" in some embodiments includes infrared reflectance oculography measurements, and hence may additionally be representative of tonic eye movement.

Technology described below includes methods for detecting or predicting a seizure in a human subject. These methods are preferably implemented by way of software instructions executing on processing equipment that is connected to blepharometric data collection hardware. The methods include operating monitoring hardware thereby to generate blepharometric data for the human subject, wherein the blepharometric data is representative of eyelid position as a function of time, and subsequently processing the blepharometric data thereby to identify a plurality of blepharometric artifacts. Processing is also performed thereby to determine either the identified blepharometric artifacts correspond to a predefined profile. For example, these profiles may be defined by logical rules (e.g., to describe data situations such as "Value for Artifact A is measured greater than B on C occasions within time D," which might be "inter-event interval of less than 30 ms record 10 times in one minute"). In the event that, for a specific time window, the identified blepharometric artifacts correspond to a predefined profile, providing an output representative of either: (i) an increased risk of a future seizure event in a time period subsequent to the specific time window; or (ii) detection of a seizure event within the specific time window. Various examples of blepharonic artifacts that may be used as the basis for profiles are discussed below. By defining rules to identify presence of profiles based on real-time analysis of blepharometric data, hardware may be configured to provide alerts substantially in real-time.

FIG. 1 illustrates a first example hardware arrangement, in the form of a head wearable unit, which, in the example of FIG. 1, takes the form of spectacles 100. These spectacles need not be functional as vision affecting spectacles (i.e., they do not necessarily include lenses, and may simply be a frame that provides a wearable mount, or other head-wearable device). Spectacles 100 include a frame 101 that is mounted to a human subject's head, an IR transmitter/receiver assembly 102 that is positioned relative to the body thereby to, in use, transmit a predefined IR signal onto the subject's eye, and receive a reflected IR signal resulting from reflection of the transmitted IR signal off the user's eye or eyelid. A sizing adjustment mechanism 103 allows for control over positioning of a nose mount portion, thereby to allow effective locating of IR assembly 102 relative to the wearer's eye. A processing unit 104 (which is optionally mounted to a spectacle arm) receives and processes the received IR signal. This processing may include:

Onboard processing, using a set of artifact detection algorithms stored a computer code on a memory unit and executed via a microprocessor. For example, raw data from IR assembly 102 is subjected to one or more pre-processing algorithms (for example, filters and the like), and an artifact detection algorithm operates to identify the presence of defined data artifacts, and provide an output signal in the case that those defined data artifacts are identified.

External processing, via a secondary processing device. In this case, raw data from IR assembly 102 is transmitted (for example, via BLUETOOTH® or another wireless communication medium) to a secondary processing device, which optionally takes the form of a smartphone. In some embodiments, an onboard processor performs preliminary processing of the raw data prior to transmission, for example, to reduce complexity and/or amount of data required to be transmitted. The secondary processing device executes a software application that includes/accesses the set of artifact detection algorithms (which are stored on a memory unit of the secondary processing device). Again, these algorithms operate to identify the presence of defined data artifacts, and provide an output signal in the case that those defined data artifacts are identified.

In both cases, there is an optional functionality whereby all or a subset of data is collected for transmission or transmitted in real-time to a server device for further analysis.

Figure 2:
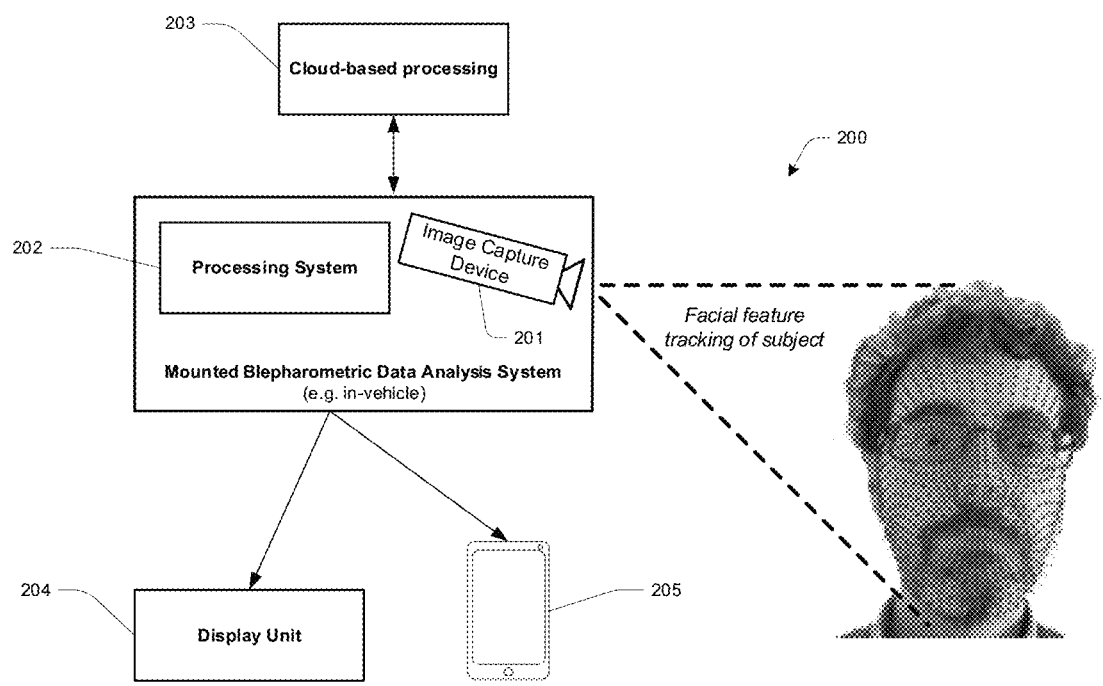
FIG. 2 illustrates a blepharometric detection system according to one embodiment.

FIG. 2 illustrates a second example hardware arrangement, in the form of a blepharometric monitoring system 200. System 200 includes a camera unit 201, which is positioned to capture image data in a region including a human subject's face, when that human subject is positioned in a defined area. For example, in some cases the defined area is an operator position for a vehicle (such as a car or truck, airline, or other, including operator and/or passenger locations). In other embodiments, the defined area is relative to a piece of furniture (for example, to allow monitoring of a subject operating a computer or watching a television), or a clinical device. The camera unit may include a webcam provided by a computer device. A processing unit 202 processes image data from camera unit 201 via a vision system thereby to identify a subject's facial region (for example, using known facial detection algorithms), and from that identify the user's eyes, and by way of image-driven tracking algorithms monitor the user's eyes thereby to detect and measure blinks (optionally in combination with cloud-based processing 203). Blinks are identified and measured thereby to determine blepharometric data, which is processed using artifact detection algorithms, for example, as discussed above. Once again, these algorithms operate to identify the presence of defined data artifacts, and provide an output signal in the case that those defined data artifacts are identified.

By way of example, in some embodiments, the hardware arrangement of FIG. 2 is installed in a vehicle, such as an automobile, and as such configured to detect artifacts in blepharometric data that are relevant to an operator of the vehicle (for example, in the context of detecting drowsiness and/or other neurological conditions).

Output, for example, in terms of alerts and the like, is delivered via an output unit such as a display device 204 (which, in a vehicle embodiment, may be an in-vehicle display) or a networked computing device (such as a smartphone 205). In some embodiments, delivery of data to an output device is provided from an Internet-based processing/data management facility to the display device rather than directly from system 200 (e.g., both are connected to a common networked data processing/management system). The output may be delivered to the human subject being monitored and/or to a third party.

Figure 3:
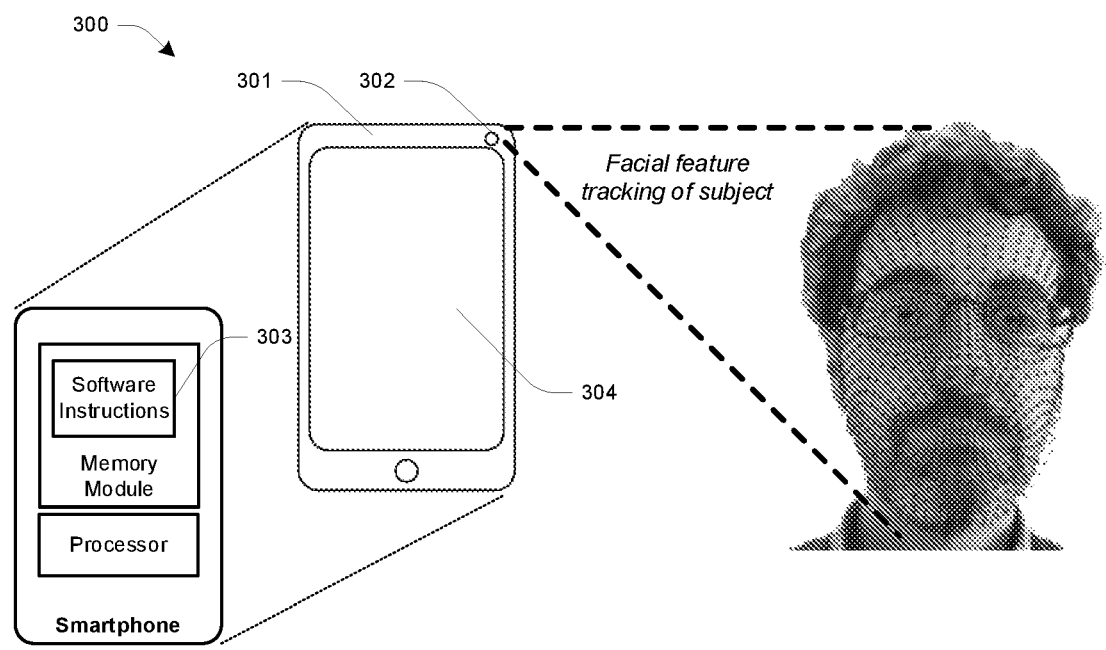
FIG. 3 illustrates a blepharometric detection system according to one embodiment.

FIG. 3 illustrates a third blepharometric monitoring system, in the form of a smartphone-integrated blepharometric monitoring system 300. From a hardware perspective, system 300 utilizes existing smartphone hardware 301. A smartphone image capture unit (preferably a front-facing camera 302, but optionally a rear-facing camera) is leveraged by a software application 303 thereby to perform facial detection and blepharometric detection/measurement in a similar manner to the embodiment of FIG. 2. In some embodiments, the software application operates as a foreground application, which delivers graphical information via the smartphone screen 304 concurrently with blink detection (in some cases this graphical information is used to assist in standardizing conditions for a blink detection period). In other embodiments, the software application operates as a background application that performs blink detection and measurement, while other software applications are presented as foreground applications (for example, blink detection while a user operates a messaging application). Processing of blink detection data is optionally performed via software application 303 using the smartphone's internal processing capabilities, transmitted to a server device for remote processing, or a hybrid approach that includes both local processing and remote processing.

Similar to the example of FIG. 3, one embodiment provides a portable electronic device including: a display screen; and a front-facing camera; wherein the portable electronic device is configured to concurrently execute: (i) a first software application that provides data via the display screen; and (ii) a second software application that receives input from the front facing camera thereby to facilitate detection and analysis if blepharometric data. For example, the first software application is, in one embodiment, a messaging application, and in another embodiment, a social media application. This allows for collection of blepharometric data while a user engages in conventional mobile device activities.

One embodiment provides computer executable code that when executed causes delivery via a computing device of a software application with which a user interacts for a purpose other than blepharometric-based data collection, wherein the computer executable code is additionally configured to collect data from a front-facing camera thereby to facilitate analysis of blepharometric data. The purpose may be, for example, messaging or social media.

Embodiments such as that of FIG. 3 provide for collection of blepharometric data via a background software application executing on electronic device with a front-facing camera. This provides opportunities to analyses a device user's neurological condition, for example, in the context of predicting seizures, advising on activities, diagnosing potential neurological illnesses, detecting drowsiness, and so on.

The precise nature of blepharometric data collected varies between embodiments, and is optionally combined with other data inputs (for example, eye movement data and/or accelerometer data). A detailed disclosure of known techniques for collecting eyelid movement data is provided in patent publications including U.S. Pat. Nos. 7,071,831, 7,791,491, 7,815,311 and US20170119248, each of which is hereby incorporated by cross reference.

Blepharometric data includes involuntary eyelid movement data from which computer processing is able to extract a range of blink attributes, also referred to herein as "blepharometric artifacts," for each of a plurality of blink events during an analysis period. The measure of blepharometric artifacts for a given blink event includes any one or more of:

- a time period from blink initiation to blink completion (also referred to as a blink duration or blink length);
- a time period between blinks, optionally measured between blink initiation times for consecutive blinks;
- analysis of "events," including relative timing of events, with an "event" being defined as any positive or negative deflection that is greater than a given velocity threshold for a given duration-a blink is defined as the pairing of positive and negative events that are within relative amplitude limits and relative position limits;
- a time period for eye closure motion;
- a time period during which the eye is closed;
- a time period for eye re-opening motion; and
- velocity measurements (which include velocity estimation measurements) for eye closure motion and/or eye re-opening motion are also made, which may be used for the purposes of determining amplitude-to-velocity ratios.

It should be appreciated that data collected depends on a number of embodiment-specific factors, including sensor hardware. For example, some measurements such as eyelid motion velocity measurements, amplitude-velocity-ratios, saccades, and the like require high resolution monitoring hardware (for example, hardware configured for infrared reflectance oculography), whereas some embodiments make use of hardware with lesser resolution capabilities (for example, smartphone front-facing camera modules, which often have a frame rate of lesser resolution than can be achieved via IR reflective oculography). It will be appreciated how various detection and processing methods are able to be achieved using hardware of varying resolution capabilities.

Seizure Prediction Using Blepharometric Data

It has been identified that blepharometric monitoring hardware as described above is able to be applied for the purposes of detecting a probability (or potential risk) of an upcoming seizure event in a human subject (for example, a seizure such as an epileptic seizure). This detection enables seizure prediction with substantial advance warning, for example, in the range of 10 minutes to one hour. For example, experimental results discussed below enabled seizure prediction around 30-40 minutes prior to a seizure. Such detection, even where prediction accuracy is imperfect (especially in terms of false-positives), is of huge value to seizure sufferers, given that conventionally it is the unpredictable nature of seizures that leads to some of the greatest challenges and dangers. Advance prediction enables a range of risk-mitigation practices to be employed, including actions intended to reduce the likelihood of a seizure (for instance, medication or behavioral modification) and actions intended to reduce the dangers of a non-prevented seizure (for example, moving the subject to a safe location, ceasing operation of machinery, and so on).

According to various embodiments, methods of predicting a threshold probability or risk of a future seizure event includes operation of blepharometric monitoring hardware thereby to detect eyelid position and enable measurement of attributes of blepharometric artifacts, processing data provided by the blepharometric monitoring hardware thereby to the detect whether or not there has been threshold periodic statistical variation from a baseline value for one or more blepharometric artifact attributes, and, in the case that such as variation is identified, provide an output signal (for example, an alert signal). A particular blepharometric artifact considered herein is eyelid movement calmness, for example, as determined via analysis of negative inter-event duration (IED), or an alternate metric associated with negative IED or eyelid movement calmness. For instance, in further examples additional artifacts are used in combination with IED, or as alternatives to negative IED, with examples including a calculation that quantifies eyelid movement degree between a blink eyelid closure motion and subsequent blink eyelid opening motion.

One embodiment includes a computer implemented method (which is optionally performed via any of the hardware arrangements FIG. 1 to FIG. 3) including receiving, as input, data derived from a sensor device that is operated to detect eyelid movements for a human subject (for example, a sensor device provided via any the spectacles of FIG. 1 or image capture device of FIG. 2 or FIG. 3).

The method additionally includes processing the input data thereby to determine a series of values representative of "eyelid movement calmness." The term "eyelid movement calmness" refers to the extent to which eyelid motion during a blink is smooth or erratic, based on measurement and analysis parameters. A metric proposed herein for measuring eyelid movement calmness is negative IED, as discussed below. Embodiments may use direct analysis of negative IED, or measurements that are otherwise representative of eyelid movement calmness. In overview, increase in eyelid movement calmness (for example, threshold spiking in IED) in some embodiments results in seizure prediction. As noted above, an event is defined as any positive or negative deflection that is greater than a given velocity threshold for a given duration (for example, are a velocity of over 10 units/second for greater than 10 milliseconds). A blink is defined as the pairing of positive and negative events that are within relative amplitude limits and relative position limits (that is, using threshold levels to demonstrate a process of adequate eye closing and re-opening).

Figure 4A:
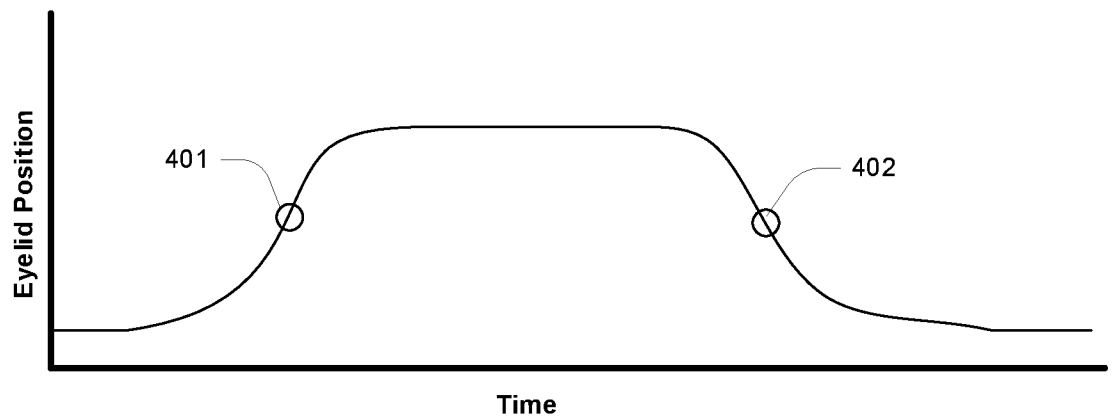
FIG. 4A and FIG. 4B illustrate eyelid movement events.

Embodiments described herein consider a measure of "negative IED." For blink events, negative IED is the time from the maximum velocity of an eye closure portion of a blink to the time of the maximum velocity of the previous event. This in effect provides a measure of eyelid movement calmness, for example, eyelid movement calmness during a blink event; for a "calm" blink event there is less irregular movement between a blink eye closure motion and blink eye opening motion. This is best shown in FIG. 4A, which shows a representative "calm" blink, and FIG. 4B, which shows a representative "non-calm" blink. In these figures, the vertical exist represents eyelid position, and the horizontal axis represents time. It will be appreciated that each figure shows a blink of similar duration.

In FIG. 4A, two events 401 and 402 are recorded. In this case, the negative IED is the time period between event 401 and event 402. This also defines a useful measure of Total Blink Duration (TBD), as events 401 and 402 represent blink eyelid closure and opening, respectively.

Figure 4B:
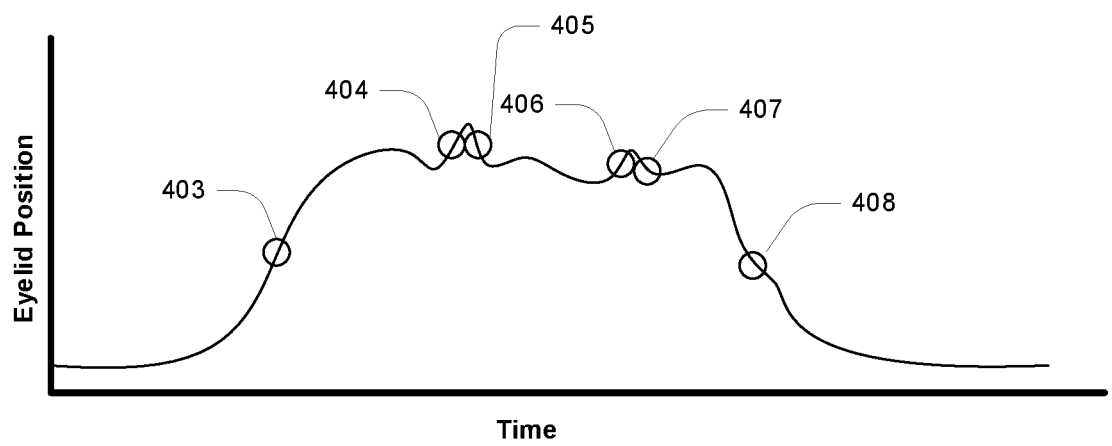

In FIG. 4B, additional erratic eyelid movements (above the detection threshold (events 404 to 407)) are apparent between a blink eyelid closure event 403 and a blink eyelid opening event 408. Here, the negative IED is the time period between event 408 and event 407 (and BTD is between events 403 and 408). It will be appreciated that, for non-calm blinks, negative IED is inherently significantly shorter than BTD, and indeed shorter in BTD than substantially any conventional blink events.

The method additionally includes identifying, in the determined series of values representative of IED, a threshold increase in negative IED characteristics. Examples of how this threshold increase is categorized are discussed below:

- Negative IED having greater than three spikes in a period of between 5 and 20 minutes (preferably between 10 and 15 minutes). A "spike" is defined optionally as either: (i) a 30% increase over historical average; or (ii) a negative IED of greater than 3000 ms. In some embodiments, a threshold of 4 spikes is applied.
- Detection of three or more events in a period of between 5 and 20 minutes (preferably between 10 and 15 minutes) where negative IED is greater than or equal to 80% of BTD.
- Determining a baseline IED periodic value for the subject, and identifying a threshold deviation from the baseline IED periodic value for the subject. For example, the baseline IED may be an average IED value over a predefined time period, with the period preferably being between 5 minutes and 20 minutes (preferably between 10 and 15 minutes). In one example the baseline negative IED periodic value for the subject is defined by an average IED value over a defined time period of over 10 minutes, and the threshold deviation is equal to or greater than 15%.
- Determining a baseline IED value for the subject, and identifying a threshold count of deviation instances (spikes) from the baseline IED value for the subject over a defined period. For example, the method may include maintaining a rolling count of IEDs over a defined threshold value for a predefined preceding period, and making a determination that the threshold increase in the case that the count exceeds a predefined value. The threshold value is in one example 200% of a calculated baseline average negative IED value, the predefined preceding period is between eight minutes and fifteen minutes, and the count is equal to or greater than four. A specific example is to identify whenever there are four IED spikes of over 200% of a baseline value in a given ten minute period.

The method also includes, in response to identification of the threshold increase in negative IED characteristics (or other measure of eyelid movement calmness), providing an output signal representative of future seizure event prediction. The nature of this output varies between embodiments, for example, based on hardware that is used. In one example using the hardware of FIG. 1, a haptic, visual and/or audible warning is provided by spectacles. Alternately, the output may be delivered via a separate device, such as a smartphone. Where the output is provided via a display screen (which may be available in any of the hardware arrangements of FIG. 1 to FIG. 3), that output optionally provides a suggestion for seizure risk mitigation measures, such as a suggestion to take medication, a suggestion to adopt a safe position, a recommendation to perform a prescribed physical activity, and so on. The hardware may also be used to detect the onset of a seizure, and in doing so in some cases determine efficacy of particular seizure risk mitigation measures such as preventative medications.

In some embodiments, the method includes identifying presence of an additional artifact in blepharometric data, wherein the step, in response to identification of the threshold increase in IED characteristics, providing an output signal representative of future seizure event prediction, is performed only in the case that the additional artifact is identified.

Discussion of Experimental Results

Blepharometric data was collected from patients in a controlled hospital setting with known (or suspected) history of epilepsy, using infrared reflectance oculography spectacles, and seizure detection was carried out using an EEG and trained medical personnel. Various algorithms are used to detect blinks and the characteristics of the blinks (from simple measures such as amplitude, duration, through to more complex measures such as amplitude-velocity ratio and inter-event duration (IED)). These are used to examine changes in the statistics of these features during baseline periods without seizures and also during the period prior to the seizure.

Figure 5:
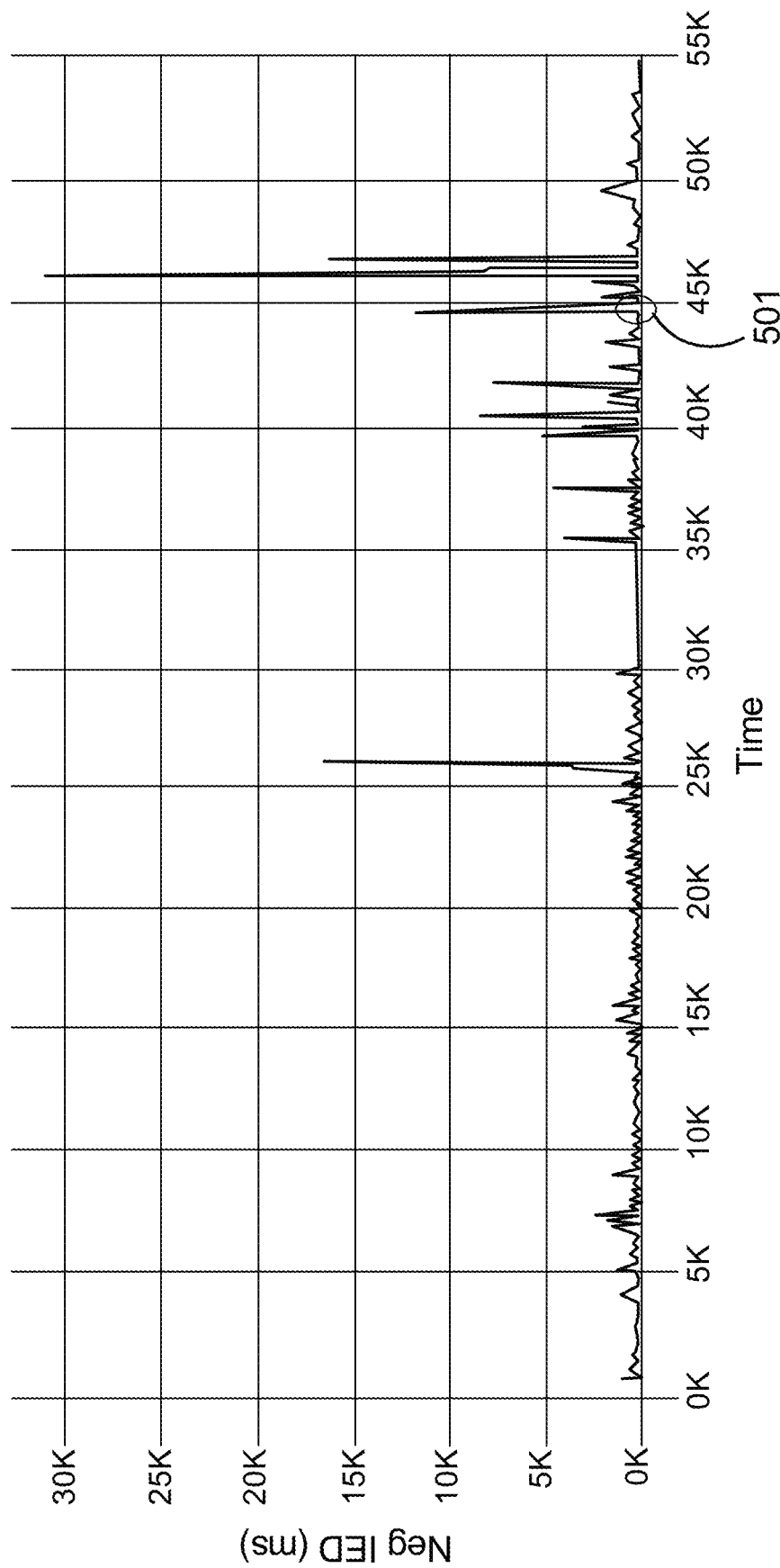
FIG. 5 illustrates spikes in negative IED associated with a seizure

FIG. 5 illustrates blepharometric data, specifically, negative IED data (on the vertical axis, with time on the horizontal axis), from a monitored subject prior, during and following a seizure. The seizure is marked by arrow 501, based on another means of seizure detection (in this example being manual medical detection using non-blepharometric means). The graph shows that, in a period of about 40 minutes prior to the seizure event, there is prolonged peaking of negative IED.

Seizure Detection Using Blepharometric Data

It has been identified that blepharometric monitoring hardware as described above is able to be applied for the purposes of detecting occurrence of a seizure event in a human subject (for example, an epileptic seizure). This enables seizure detection that is effective for many non-convulsive/absence seizures, which are often unnoticed by known seizure detection hardware (for example, accelerometer-based hardware). This ability enables a better understanding of human subjects and seizure-related risk factors. For example, in some subjects, non-convulsive or absence seizure might otherwise go unnoticed, potentially miscategorized as "daydreaming" or the like.

According to various embodiments, methods of detecting a seizure event include operation of blepharometric monitoring hardware thereby to detect blinks and enable measurement of attributes of blepharometric artifacts, processing data provided by the blepharometric monitoring hardware thereby to the detect whether or not there has been threshold periodic statistical variation from a baseline value for one or more blepharometric artifact attributes, and, in the case that such as variation is identified, provide an output signal (for example, an alert signal).

Example: Myoclonic Motion

A particular blepharometric artifact considered herein is myoclonic eyelid motion. This is categorized by an increase in blink event rate, interposed by partial openings. That is, from a plain-language perspective, myoclonic eyelid motion is typically categorized by an increased rate of blinks where the subject's eyes do not fully open between blink events.

One embodiment includes a computer implemented method (which is optionally performed via any of the hardware arrangements FIG. 1 to FIG. 3) including receiving, as input, data derived from a sensor device that is operated to detect eyelid movements for a human subject (for example, a sensor device provided via any the spectacles of FIG. 1 or image capture device of FIG. 2 or FIG. 3).

The method additionally includes processing the input data thereby to determine blepharometric artifact attributes in some embodiments including metrics representative of: (i) blink rate; and (ii) eyelid closure extent. For example, such metrics are able to be extracted from data that records eyelid position as a function of time based on IR and/or image-based monitoring techniques.

The method additionally includes identifying, in the eyelid movement data, a threshold statistical deviation in monitored attributes that is representative of myoclonic eyelid motion. Examples of how this threshold statistical deviation is identified discussed below:

An increase in average closure over a defined period, combined with a blink event rate of greater than a defined threshold. The defined threshold is preferably greater than 1 blink per second, sustained for at least three seconds, with an average closure of over 50%.

Identification of a threshold number of blink events in a defined period with less than threshold eye re-opening. For example, in one embodiment, the threshold number of blinks is between four and six in a defined period of between 2 and 8 seconds, with less than 50% eye opening. In one example, this is set to six blinks in three seconds with no opening beyond 50%.

One embodiment employs an approach whereby an eyelid motion signal is processed thereby to derive a first derivative, and from that a peak and trough detector is applied to identify zero velocity spots. These zero velocity spots enable calculation of blink rate, or otherwise a number of blinks over a defined period. This is combined with eyelid position from the eyelid motion signal thereby to identify a combination of: (i) blink rate above a defined threshold (preferably greater than one blink per second); (ii) sustained for a defined period (preferably greater than 3 seconds); and (iii) with less than 50% eyelid opening.

The method also includes, in response to identification of the threshold statistical deviation in monitored attributes that is representative of myoclonic eyelid motion, providing an output signal representative of seizure detection. The nature of this output varies between embodiments, for example, based on hardware that is used. In one example using the hardware of FIG. 1, a haptic, visual and/or audible warning is provided by spectacles. Alternately, the output may be delivered via a separate device, such as a smartphone (including a smartphone or secondary device that receives the alert via networked communications, for example, in the context of warning a carer or other third party of a seizure event).

In some embodiments, the method includes identifying presence of an additional artifact in blepharometric data, wherein the step, in response to identification of the threshold increase in statistical deviations indicative of myoclonic eyelid motion, providing an output signal representative of future seizure event prediction, is performed only in the case that the additional artifact is identified.

Discussion of Experimental Results: Myoclonic Motion

Blepharometric data was collected from patients in a controlled hospital setting with known (or suspected) history of epilepsy, using infrared reflectance oculography spectacles, and seizure detection was carried out using an EEG and trained medical personnel. Various algorithms are used to detect blinks and the characteristics of the blinks (from simple measures such as amplitude, duration, through to more complex measures such as amplitude-velocity ratio and inter-event duration (IED)). These are used to examine changes in the statistics of these features during baseline periods without seizures and also during the period prior to the seizure.

Figure 6A:
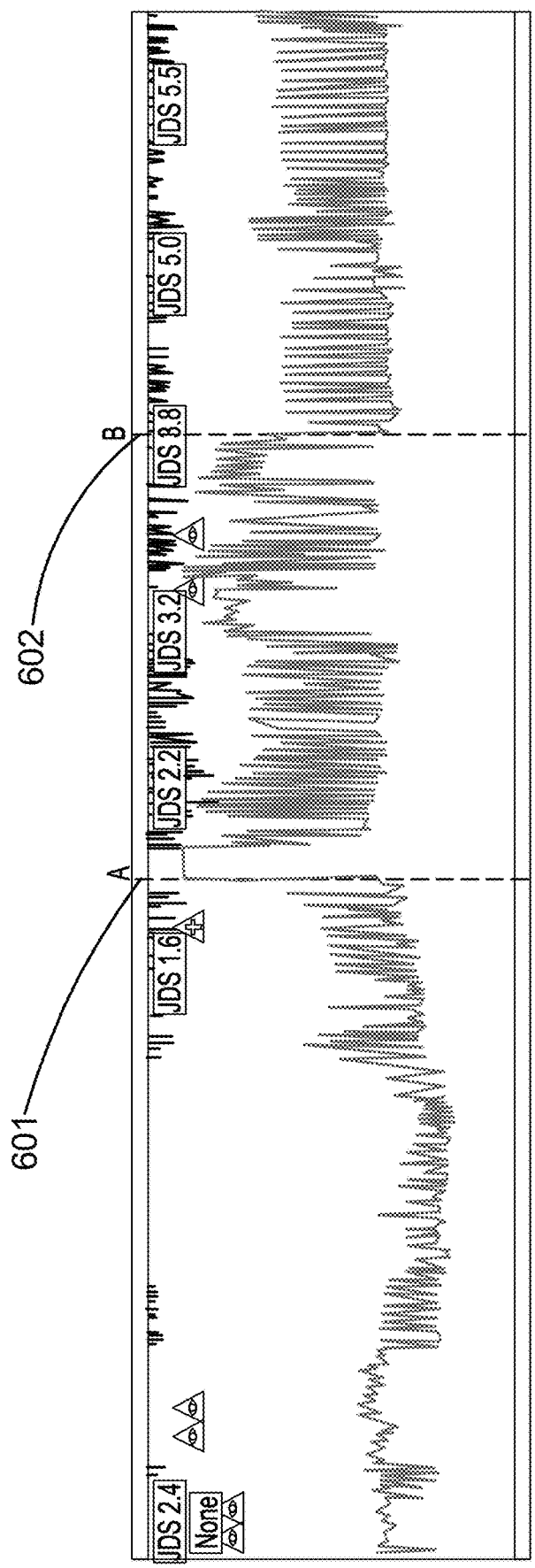
FIG. 6A and FIG. 6B illustrate blepharometric data corresponding with seizure events.

FIG. 6A illustrates blepharometric data, specifically, eyelid movement data, from a monitored subject prior, during and following a seizure. The seizure is marked by arrow markers 601 (start time) and 602 (end time), as determined by a separate EEG signal.

Figure 6B:
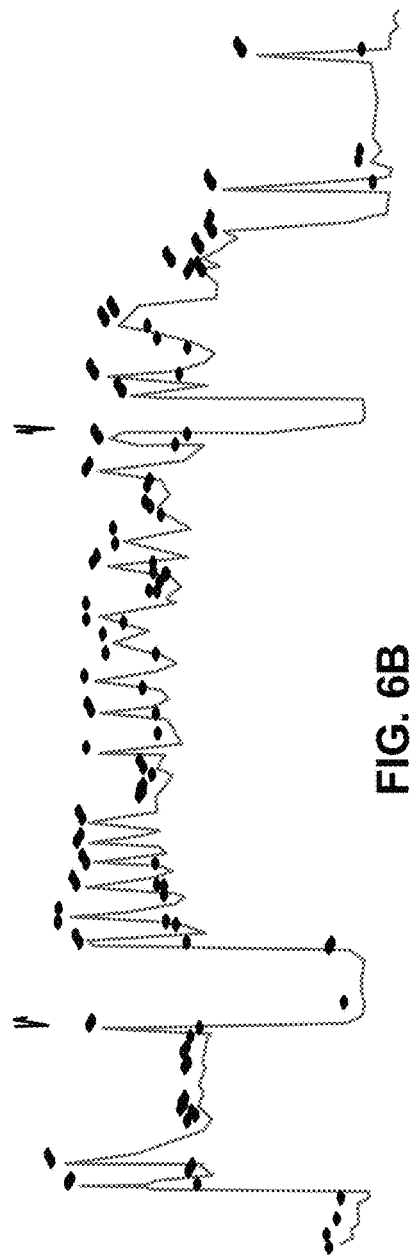

FIG. 6B provides an expanded view of the data of FIG. 6A around the seizure event, where Myoclonic eyelid motion is clearly visible, in the sense that eyelid position does not return to full opening (lower on the vertical axis) between a series of blinks.

Example: Inter-Blink Pedestal

In some embodiments, a system is configured to monitor for blepharon artifacts that represent an inter-blink pedestal. More specifically, processing of blepharometric data collected via infrared reflectance oculography techniques is performed thereby to determine whether there is data representative of a series of blink events within a threshold period (preferably less than ten seconds) with a temporary inter-blink pedestal. An inter-blink pedestal is a data artifact that is representative of an increased inter-blink amplitude, which persists for a series of blinks (for example, between three and ten blinks), before inter-blink amplitude returns to a preceding baseline range.

Figure 7A:
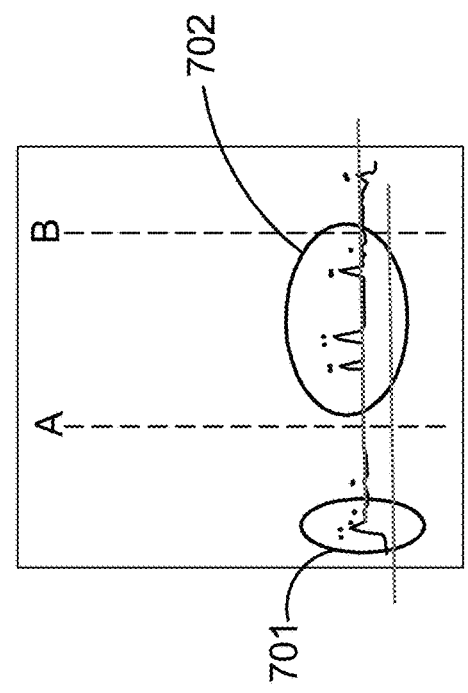
FIGS. 7A-7C illustrate blepharometric data corresponding with absence type seizure events.
Figure 7B:
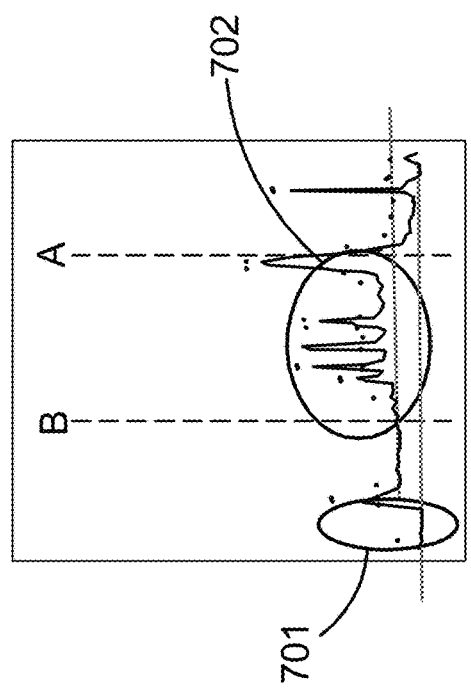
Figure 7C:
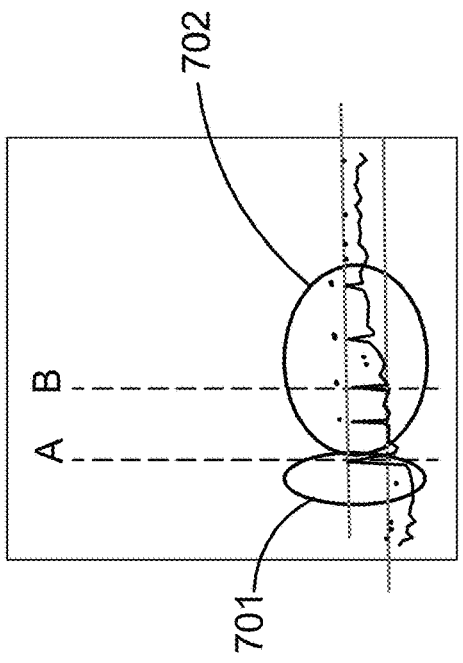

Examples are shown in FIGS. 7A, 7B and 7C, with each showing an initial blink (in circle 701) prior to which a reflectance-based measure of inter-blink amplitude is within a regular baseline range, and after which inter-blink amplitude measures (circle 702) are in a pedestal range that is greater than the regular baseline range. Experimental results show that this pedestal range is due to tonic eye motion.

Experimental data has shown that detection of an inter-blink pedestal may be used to predict presence of absence type seizures. These seizures are subtle and short-lived, making them difficult to detect using conventional methods. However, they can be especially dangerous, for example, where a person is operating a vehicle or machinery. Hence configuring blepharometric monitoring technology to detect presence of inter-blink pedestals provides a particularly useful means of managing seizure risks.

Example: AVR Asymmetry

In some embodiments, a system is configured to monitor for blepharon artifacts that represent AVR asymmetry. Specifically, blepharometric data processing modules are configured to identify blepharometric artifacts correspond that to an increase in positive AVR and decrease in negative AVR for a series of blinks within a five second period during the specific time window. This series of blinks may comprise between two and ten blinks at a frequency of between two and five blinks per second (i.e., at a frequency of 2-5 Hz). Experimental results have shown that such a profile in blepharometric data is representative of a seizure, such as an epileptic seizure.

Figure 8:
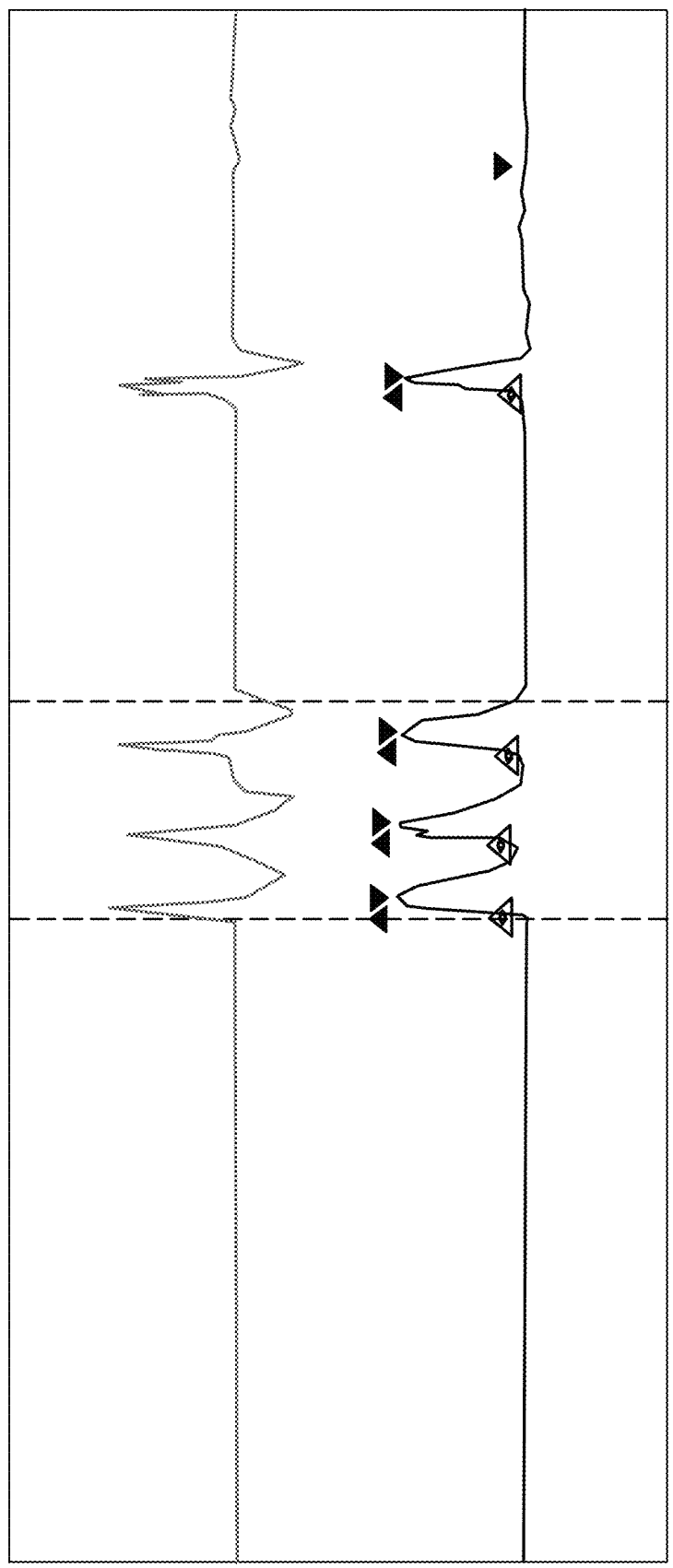
FIG. 8 illustrates blepharometric data corresponding with a seizure event, showing AVR asymmetry.

FIG. 8 shows example experimental data corresponding to a seizure event. The data shows two plots: an upper plot of velocity against time, and a lower plot of amplitude against the same time axis. This shows a series of three blinks over a period of 700 milliseconds, corresponding to a seizure, followed by a further blink. The blinks in the series display AVR asymmetry, whereas the subsequent blink does not. For the series of blinks, the AVR characteristics were as follows:

Blink 1: Positive AVR-1.043; Negative AVR-2.330
BLINK 2: Positive AVR-1.087; Negative AVR-2.173
Blink 3: Positive AVR-1.076; Negative AVR-2.089

As reference, typical AVR values are: Positive AVR 1.3, and Negative AVR 1.6.

Example: Sudden Decrease in Blink Frequency

Figure 9:
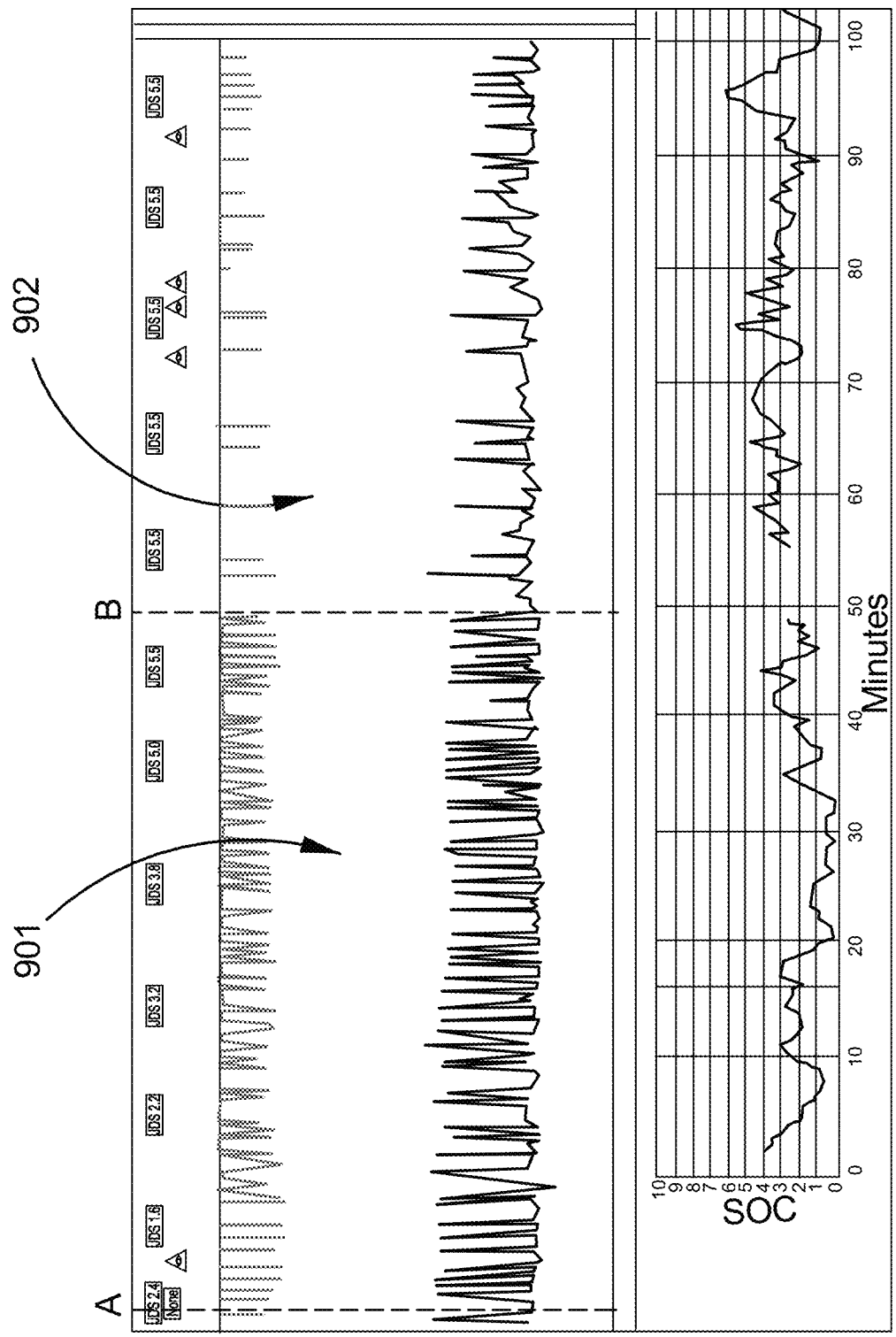
FIG. 9 illustrates blepharometric data corresponding with an epileptic seizure event, showing a sudden decrease in blink frequency.

In a further embodiment, blepharometric processing technology is configured to monitor for a sudden decrease in blink frequency by about 50%. For example, this is shown in FIG. 9, which shows a sudden decrease in blink frequency between a seizure region 901, and post-seizure region 902. This is especially useful in the context of, for example, configuring technology to provide an alert in the case that a subject has experienced a seizure.

Conclusions and Interpretation

It will be appreciated that the above disclosure provides analysis methods and associated technology that enables improved advance prediction of seizure events in a human subject.

It should be appreciated that in the above description of exemplary embodiments of the present disclosure, various features of the present disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B that may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The invention claimed is:

1. A method for predicting a seizure in a human subject, the method including:
    operating monitoring hardware thereby to generate blepharometric data for the human subject, wherein the blepharometric data is representative of eyelid position as a function of time;
    identifying blink events in the blepharometric data;
    processing the blepharometric data thereby to identify a plurality of blepharometric artifacts for each detected blink event; and
    in the event that, for a specific time window, the identified blepharometric artifacts correspond to a predefined profile, providing an output representative of an increased risk of a future seizure event in a time period subsequent to the specific time window, wherein the human subject is not identified to be experiencing a seizure event during the specific time window;
    wherein the identified blepharometric artifacts correspond to the predefined profile in the event that the identified blepharometric artifacts demonstrate a threshold measure of abnormal blink eyelid movement calmness during the specific time window, wherein eyelid movement calmness is quantified relative to the extent to which eyelid motion is smooth or erratic.

2. The method of claim 1, wherein the threshold measure of abnormal blink calmness is derived from measurements of inter-event durations.

3. The method of claim 1, further comprising:
    determining a baseline eyelid movement calmness periodic value for the subject; and
    identifying a threshold deviation from the baseline eyelid movement calmness periodic value for the subject.

4. The method of claim 1, wherein the predefined profile represents whether eyelid motion during a change in eyelid position is smooth or erratic.

5. A method according to claim 1, wherein the identified blepharometric artifacts correspond to a predefined profile in the event that there is detection of a threshold number of spikes in blink calmness measurements during the specific time window.

6. A system configured to detect or predict a seizure in a human subject, the system including:
    monitoring hardware configured to generate blepharometric data for the human subject, wherein the blepharometric data is representative of eyelid position as a function of time; and
    a processing unit configured to process the blepharometric data thereby to identify a plurality of blepharometric artifacts, and, in the event that, for a specific time window, the identified blepharometric artifacts correspond to a predefined profile, providing an output representative of an increased risk of a future seizure event in a time period subsequent to the specific time window, wherein the subject is not identified to be experiencing a seizure event during the specific time window;
    wherein the identified blepharometric artifacts correspond to the predefined profile in the event that the identified blepharometric artifacts demonstrate a threshold measure of abnormal blink calmness during the specific time window, wherein eyelid movement calmness is derived from a measurement representative of eyelid movement during a detected blink event based on a quantity of irregular movement between a blink eye closure motion and blink eye opening motion.

7. The system of claim 6, wherein the threshold measure of abnormal blink calmness is derived from measurements of inter-event durations.

8. The system of claim 6, wherein the processing unit is configured to perform a method including:
    determining a baseline eyelid movement calmness periodic value for the subject; and
    identifying a threshold deviation from the baseline eyelid movement calmness periodic value for the subject.

9. The system of claim 6, wherein the identified blepharometric artifacts include artifacts representative of time durations between blink events.

10. A system according to claim 6, wherein the identified blepharometric artifacts correspond to a predefined profile in the event that there is detection of a threshold number of spikes in blink calmness measurements during the specific time window.

11. A computer-implemented method for performing prediction of a change in neurological conditions for a human subject, the method including:
    receiving, as input, data derived from a sensor device that is operated to detect eyelid movements for a human subject;
    processing the input data thereby to determine a series of values representative of eyelid movement calmness, wherein eyelid movement calmness is derived from a measurement representative of eyelid movement during a detected blink event based on a quantity of irregular movement between a blink eye closure motion and blink eye opening motion;
    identifying, in the determined series of values representative of eyelid movement calmness, a threshold increase in eyelid movement calmness characteristics over a defined period of time; and in response to identification of the threshold increase in eyelid movement calmness characteristics, providing an output signal representative of a change in neurological conditions.

12. The method of claim 11, wherein eyelid movement calmness is derived from measurements of negative IED.

13. The method of claim 12, wherein negative IED trends toward Blink Total Duration (BTD) as eyelid movement calmness increases.

14. The method of claim 11, wherein calmness is derived from measurements of eyelid movement between a detected blink eyelid closure event and a subsequent blink eyelid opening event.

15. The method of claim 11, wherein threshold eyelid movement calmness is represented by observation of below a threshold of eyelid movement between a detected blink eyelid closure event and a subsequent blink eyelid opening event.

16. The method of claim 11, wherein identifying, in the determined series of values representative of eyelid movement calmness, a threshold increase in eyelid movement calmness characteristics, includes: determining a baseline eyelid movement calmness periodic value for the subject, and identifying a threshold deviation from the baseline eyelid movement calmness periodic value for the subject.

17. The method of claim 16, wherein the threshold deviation is represented by detection of a threshold number of spikes in blink calmness measurements in a defined period.

* * * * *